United States Patent [19]

Arginteanu

[11] Patent Number: 5,776,463

[45] Date of Patent: Jul. 7, 1998

[54] METHOD OF REDUCING STRESS AND CIRCULATORY HEART DISEASE WITH FREEZE-DRIED BORAGE PETAL EXTRACTS

[76] Inventor: Ronit Arginteanu, 401 E. 86th St. Apt. 9G, New York, N.Y. 10028

[21] Appl. No.: 802,069

[22] Filed: Feb. 19, 1997

[51] Int. Cl.⁶ .............................. A61K 35/78; A23F 3/34; A23F 3/00

[52] U.S. Cl. ................... 424/195.1; 426/384; 426/435; 426/597

[58] Field of Search .................... 424/195.1; 426/77, 426/78, 384, 418, 419, 431, 435, 597

[56] References Cited

U.S. PATENT DOCUMENTS

| | | | |
|---|---|---|---|
| 4,317,816 | 3/1982 | Arichi et al. | 424/182 |
| 4,427,694 | 1/1984 | Benecke et al. | 424/282 |
| 4,755,504 | 7/1988 | Liu | 514/26 |
| 4,767,626 | 8/1988 | Cheng | 424/195.1 |
| 4,774,229 | 9/1988 | Jordan | 514/25 |
| 4,774,343 | 9/1988 | Namiki et al. | 549/435 |
| 4,859,468 | 8/1989 | Kubo et al. | 424/195.1 |
| 4,981,844 | 1/1991 | Alexander et al. | 514/21 |
| 5,055,446 | 10/1991 | Alexander et al. | 514/2 |
| 5,166,139 | 11/1992 | Bombardelli | 514/26 |
| 5,214,062 | 5/1993 | Mark et al. | 514/369 |
| 5,229,136 | 7/1993 | Mark et al. | 424/535 |
| 5,397,778 | 3/1995 | Forse et al. | 514/198 |

OTHER PUBLICATIONS

Grieve, A Modern Herbal, The Medicinal, Culinary, Cosmetic and Economic Properties, Cultivation and Folklore of Herbs, Grasses, Fungi, Shrubs and Trees with All Their Modern Scientific Uses, Barnes & Noble Inc., NY, NY, pp. 119-120, 1996.

Remington's Pharmaceutical Sciences, 18th Ed., Mack Publishing Co., Easton PA, pp. 1483-1484, 1980.

*Primary Examiner*—David M. Naff
*Assistant Examiner*—Janet M. Kerr
*Attorney, Agent, or Firm*—Imre Balogh

[57] ABSTRACT

Oral pharmaceutical compositions containing petals of borage or extract of borage petals and method for the prevention and treatment of stress and circulatory heart diseases in a mammal by administration of the compositions.

6 Claims, No Drawings

METHOD OF REDUCING STRESS AND CIRCULATORY HEART DISEASE WITH FREEZE-DRIED BORAGE PETAL EXTRACTS

BACKGROUND OF THE INVENTION

1. Field of the Invention

The present invention relates to a method of treating circulatory heart diseases and related conditions. More particularly, the invention relates to compositions of borage used for the prevention or control of stress, and consequently, for the prevention and/or treatment of circulatory heart diseases.

2. Reported Developments

Stress and strain have long been used to denote conditions in patients caused by psychological and emotional influences. It is recognized that emotional stress and strain could cause considerable physiological alterations and as such cause medical problems.

The central nervous system controls the cardiovascular activity, and during stress, considerable alteration of the cardiovascular activity may occur, such as palpitation, arrhythmia, angina and hypertension as well as symptoms, such as shortness of breath, chest pain and emanating shoulder pain. During non-stressful periods cardiovascular activity is matched to concurrent metabolic need. When a situation is perceived as threatening or stressful, however, the central nervous systems takes over and exerts its influence on the cardiovascular system via the endocrine system and by overriding normal antonomic functioning.

The influence of the central nervous system over the cardiovascular system during threatening situations may result in stress, angina, palpitations and hypertension.

Stress is generally defined as feeling emotionally or physically threatened and feeling an inability to counteract the threat. A "fight-of-flight" response is triggered in the body, which sends a signal to the brain which, in turn, activates the sympathetic nervous system to produce stress hormones such as adrenalin and nonadrenalin. These hormones increase heart rate, blood pressure and breathing to send more blood and oxygen to the parts of the body that need it, such as muscles in the arms and legs so that the person can flee the danger. Once the person is out of danger, the nervous system produces hormones, such as acetylcholine, to counteract these effects resulting in "calming down".

The physiologic response or "fight-of-flight" response may be triggered by small or large influences exerted on the person by the environment and is typically repetitive in modern societies. If stress becomes chronic, a person produces abnormal levels of stress hormones. From repeatedly elevated blood pressure the arteries stiffen and the heart weakens from over-exertion. As a result, heart enlargement can occur.

Healthy artery walls can counter the effects of stress through their inner lining or endothelium, which secretes nitric oxide to expand the arteries so more blood can reach the heart during times of stress. But if a person's arteries become distressed, the endothelium produces less nitric oxide during stress, when hormones constrict blood vessels, and the nitric oxide loses its effectiveness. The result is ischemia, decreased blood flow to the heart, often causing chest pains called angina.

Angina is a painful muscle spasm indicating that the heart is not getting sufficient blood. It often manifests itself as a severe constriction in the chest, sometimes associated with pains in one or both shoulders or arms which may also radiate to the back or jaw. The pain and constriction is usually increased by physical effort and relieved by rest. Angina may also be provoked by feelings of anger, anxiety and excitement.

Palpitations is the symptom of the heart beating faster or more intensely than normal. This sensation of pounding in the chest can be the result of a rapid heartbeat, or an irregular heart rate. Palpitations usually occur in self-limiting episodes lasting from several minutes to hours.

Two major factors causing high blood pressure or hypertension are stress and arteriosclerosis. Blood travels through the body in the arteries. These vessels are constantly under pressure as the blood moves through them. The heart's pumping action drives the blood forward, creating pressure. Each heartbeat pushes the pressure in the arteries upward. The pressure reaches a peak, and then it drifts back down to a minimum level. The next heartbeat pushes the pressure up once again.

The highest pressure in the arteries, achieved at the peak of the heart's pumping, is called the systolic pressure. The lowest pressure, just before the next heartbeat, is called the diastolic pressure. As total blood pressure increases, both the systolic and diastolic numbers can increase. However, the diastolic number is considered more important, since it represents the pressure in the arteries when the heart is the most relaxed. When the diastolic number is elevated, there is more likely to be a real problem with the circulation of blood, since such increased numbers indicate that even when the heart is relaxed the pressure in the blood vessels is too high.

It is believed that cardiovascular reactivity to stress plays a definite role in the development of sustained arterial hypertension.

The prior art has provided medications and treatments for the cause or symptoms of circulatory heart diseases. The present invention provides compositions and methods for the prevention and/or control of stress and associated circulatory heart diseases by using borage, a naturally occurring plant which was surprisingly found to have beneficial activity for such prevention and treatment without certain side effects associated with certain synthetic compounds/compositions used by the prior art.

Borage (Boraginacae, Borago officinalis) has been known at least since the seventeenth century and has been used medicinally to treat conditions, such as melancholic states, coughs and depression. Other uses of borage along with other herbs included: culinary use to flavor ready-made alcoholic beverages such as wine cups; and flavoring in food, such as salads. Borage was also used as a source of gamma linoleic acid. The constituents of borage include mucilage, tannin, essential oils, potassium, calcium, pyrrolizioline all alkaoids and gamma linoleic acid. U.S. Pat. No. 5,397,778 discloses an enteral formulation for the treatment of inflammation and infection. The formulation contains saponin as the main ingredient. Other ingredients containing high levels of polyunsaturated fatty acids, such as fish oils, flax oil, borage oil, black current seed oil, cannola oil and rapeseed oil may be used in combination with saponin for the treatment of inflammation and infection.

An object of the present invention is to provide convenient and stable formulations of borage for the prevention and/or treatment of stress.

Another object of the present invention is to provide a method for the prevention and treatment of stress using the formulations of the present invention.

Still another object of the present invention is to provide a method for the prevention and treatment of circulatory heart diseases including angina, palpitations and hypertension.

SUMMARY OF THE INVENTION

In accordance with one aspect of the present invention, oral formulations of borage petals or their extracts are provided in pharmaceutically acceptable vehicles. The pharmaceutically acceptable vehicles are selected from the group consisting of water, beverages, tablets, capsules, medicinal drops and aqueous/alcoholic vehicles.

In another aspect of the present invention, a method for prevention and treatment of stress and stress-associated circulatory heart diseases of angina, palpitations and hypertension is provided by administering to a mammal in need of such prevention and treatment an effective stress-preventing or stress-relieving amount of borage petals or extract thereof in pharmaceutically acceptable vehicles.

Preferred compositions comprise freeze dried extracts of borage petals.

Still more preferred compositions comprise freeze dried extracts of borage petals which are reconstitutable with water and used as medicinal drops in beverages.

DETAILED DESCRIPTION OF THE PRESENT INVENTION

In preparing a borage-containing formulation of the present invention, petals of the flowering borage plants are collected when the plants are in full bloom. While the petals could be used immediately when freshly collected, they do not keep well but rapidly deteriorate. It was found that freeze drying maintains the ingredients in the petals without the petals losing their efficacy for the intended uses. Freeze drying of the petals can be accomplished in a conventional manner. The freeze drying can be effected in bulk after which the desired amount of petals are packed in a primary porous paper, woven or non-woven bag which then is placed in a secondary plastic bag or other container and vacuum-sealed. Alternatively the freshly picked petals can be packaged in the porous paper, woven or non-woven bag, freeze dried in the bag and then vacuum packed in an air impervious secondary plastic bag or container.

The freeze dried borage petals are used as tea by soaking the porous bag in hot water and decanting the resulting borage extract into cups.

A preferred way of preparing a borage-containing formulation of the present invention is to freeze dry the petals of the borage flowers in bulk and comminuting the same into small particles by grinding. The ground petals are then packaged into porous paper, woven or non-woven primary bags which are then placed in a secondary vacuum sealed plastic bag or container.

Preferably, the vacuum sealed borage, whether in freeze dried petal form or ground particulate form, is kept at cool temperatures or refrigerated for the provision of good shelf-life.

A still more preferred way of making a borage formulation of the present invention is by extracting the fresh or freeze dried petals of borage. Extracting is accomplished by the use of aqueous ethanol having a ratio of about 5 to 80% v/v ethanol and 95 to 20% v/v water. Following the extraction the aqueous ethanol is evaporated or vacuum distilled leaving the residual ingredients of the borage in the evaporating container or vacuum distillation apparatus. The residual ingredients are then concentrated to dryness.

Another method of obtaining an extract of borage comprises the steps of:

comminuting fresh borage petals to small particle size of 100 micron or less;

heating, at a low heat, the comminuted particles until a slight color change occurs in the particles;

mixing the particles with an organic solvent, such as acetone, methylethylketone, diethylketone, ethanol or methanol;

allowing the mixture to stand at a low temperature, such as at room temperature, to dissolve soluble compounds from the particles;

separating the extract from the unsolvated material by filtration; and evaporating or distilling the solvent to obtain the desired extract of borage.

Alternatively, the comminuted particles of borage can be mixed with hot methanol or hot ethanol to accelerate the dissolution process.

The extract of borage can be made into pharmaceutical compositions.

The pharmaceutical compositions for the convenience of the patient may be in the form of liquid dosage forms, tablets, pills, capsules, powders, solutions, suspensions, candy bars, chewing gums, syrups and beverages.

Another form of the pharmaceutical formulations of the present invention is an easily reconstitutible, freeze dried extract of the borage petals intended for use as medicinal drops used in beverages, such as tea and wine. The process comprises the steps of:

making an aqueous solution of the extract of borage petals;

mixing excipients, such as stabilizers, buffers and bulking agents into the aqueous solution;

freeze drying the so-obtained solution at a temperature of from about 40° C. to −20° C.; and vacuum drying the freeze dried composition.

Excipients may include acetic acid, citric acid, lactic acid, sodium hydroxide, sodium chloride, sucrose, and mannitol which serve as buffering and stabilizing agents. The freeze dried composition is packaged into vials and the vials are stoppered with a closure means which contains an eye dropper. Prior to use, the product is reconstituted with water and the required number of drops is added to a beverage, such as tea or wine to be consumed.

It is preferred that a compositions of the invention is in the form of a unit dose. The unit dose form of tablets or capsules contain conventional excipients, such as:

binding agents, such as acacia, gelatin, sorbitol and polyvinylpyrrolidone;

fillers, such as lactose, sugar, maize-starch, calcium phosphate, sorbitol and glycine;

tabletting lubricants, such as magnesium stearate;

disintegrants, such as starch, polyvinylpyrrolidone, sodium starch glycollate and microcrystalline cellulose; and wetting agents, such as sodium lauryl sulphate.

The solid oral compositions may be prepared by conventional methods of blending, filling, tabletting, and the like. The tablets may be coated according to methods well known in the art.

Oral liquid preparations may be in the form of emulsions, syrups, or elixirs, or may be presented as a dry product for reconstitution with water or other suitable vehicle before use. Such liquid preparations may contain conventional additives. For example, suspending agents, such as sorbitol, syrup, methyl cellulose, gelatin, hydroxyethylcellulose, carboxymethylcellulose, aluminum stearate gel, or hydrogenated edible fats; emulsifying agents, such as sorbitan monooleate or acacia; non-aqueous vehicles (which may include edible oils), such as almond oil, fractionated coconut oil, oily esters selected from the group consisting of glycerine, propylene glycol, ethylene glycol, and ethyl alcohol; preservatives, for instance methyl para-hydroxybenzoate, ethyl para-hydroxybenzoate, n-propyl parahydroxybenzoate, or n-butyl parahydroxybenzoate or sorbic acid; and, if desired, conventional flavoring or coloring agents.

A variety of methods for preparing dosage forms are found, for example, in Remington's Pharmaceutical Sciences, Mack Publishing Company, Easton, Pa. latest edition.

The broad aspect of the invention encompasses prevention and treatment of stress and associated circulatory heart diseases by using a "therapeutically effective amount" of the composition contained in the petals of borage or an extract thereof sufficient to induce a desired biological result. The result is the alleviation of the signs, symptoms or causes of the conditions described under Reported Developments. The amount of the extract of borage petals administered is dependent on the subject being treated, the severity of the condition, age and associated factors. However, an effective dose of the extract is in the range of 5 to 100 gm/kg/day, preferable about 25 to 60 gm/kg/day. The composition is administered orally twice a day or more often if symptoms of stress conditions continue to persist.

The following are non-limiting, illustrative examples for dosage unit forms of the present invention.

Example 1: Capsules 20 grams of the extract, 7 grams sodium lauryl sulfate, 50 grams starch, 50 grams lactose, 0.5 grams colloidal silicone dioxide, and 1.2 grams magnesium stearate were stirred together. The resulting mixture was filled into suitable hardened gelatin capsules, each comprising 10 grams of the extract.

Example 2: Film-Coated Tablets
Preparation of Tablet Cores 1000 grams of the extract, 5700 grams lactose and 2000 grams of starch were mixed and then humidified with a solution of 50 gram sodium dodecyl sulfate and 100 grams polyvinylpyrrolidone in about 2000 milliliters of water. The wet powder mixture was sieved and dried. Then there was added 1000 grams of microcrystalline cellulose and 150 grams hydrogenated vegetable oil. The components were mixed well and compressed into tablets, each tablet containing 50 grams of the borage extract.
Coating To a solution of 100 grams methyl cellulose in 750 milliliters of ethanol there was added a solution of 50 grams of ethyl cellulose in 1500 milliliters of dichloromethane. Then there was added 750 milliliters of dichloromethane and 25 milliliters 1,2,3-propanetriol. 100 grams of polyethylene glycol was meted and dissolved in 750 milliliters dichloromethane. This solution was added to the former solution and then there were added 25 grams of magnesium octadecanoate, 50 grams of polyvinylpyrrolidone and 300 milliliters of a concentrated color suspension (Opaspray K-1-2109®), followed by homogenization of the mixture. The tablet cores were then coated with the mixture in a coating apparatus.

Example 3: Oral Drops 500 grams of the borage extract was dissolved in 0.5 liters of 2-hydroxypropanoic acid and 1.5 liters of polyethylene glycol at 50° to 90° C. After cooling to 30° C. to 40° C., there were added 3.5 liters of polyethylene glycol and the mixture was stirred. Then there was added a solution of 1750 grams of sodium saccharine in 2.5 liters of water and, with stirring, there were added 2.5 liters of cocoa flavor and polyethylene glycol to q.s. to a volume of 25 liters, providing an oral drop solution comprising 20 milligrams of the borage extract per milliliter.

Example 4: Tea Composition 150 grams of freeze dried, vacuum packed borage petal were transferred into a covered glass container, 4 oz. (1 cup) of boiling water was added to the container and heated for 15 to 20 minutes. The petals were filtered leaving the liquid tea ready for consumption.

Compositions of the present invention were tested in vivo on volunteer patients. Objective data was obtained counting heart rate via counting pulses at the wrist using a stopwatch and measuring blood pressure with a sphygmomanometer. Subjective data was obtained from the comments of the patients prior to and subsequent to consumption of a formulation.

Heart rate and blood pressure were measured prior to testing the composition and subsequently to administration of the composition.

The subjects' heart rates and blood pressures were monitored and documented at rest in a stress-free environment. Next, the subjects were tested using two kinds of video games. Each subject was tested twice using each of the two games once. During the playing of the video games and after completing the playing each of the subjects was monitored again.

One of the video games was a tennis and handball video game (Super Pong) which has a considerable cardiovascular impact on the player. In his game each player attempts to score a goal with an electronic ball.

The other video game was the Space Invaders where the subject has command of a spaceship that is to be used to try to destroy an encroaching space craft. The subject must destroy the enemy craft before the barrage of oncoming missiles destroys his or her own spaceship, leaving the Earth without defense and subject to ravaging. The pace of the game increases as the subject performs better, and the higher the level of the skill, the more difficult the game becomes.

These two laboratory tasks adequately elicited changes in the subjects' cardiovascular activity.

Sixty patients were tested using the tea composition of Example 4. The patients were divided into three groups of 20 each, labeled A,B, and C.

Group A complained of the following symptoms on a regular basis (occurred between 1 and 4 times a week): chest pains traveling down to the shoulders and arms, angina, shortness of breath, sporadic and intense heart palpitations and numbness in fingers. They were instructed to take the tea with the onset of such symptoms. With respect to each patient, all symptoms completely disappeared within ½ hour of consumption of the tea.

Group B suffered from irregular heart beats or arrhythmia. They also consumed the tea of Example 4. Again, with respect to each patient, all symptoms were completely remedied within ½ hour of consumption of the tea. Patients also reported feeling deeply relaxed, their problems with insomnia diminished with no addictive feelings associated with the consumption.

Group C suffered from general symptoms of anxiety. We subjected them to stress research, by creating a situation that people appraise as stressful, to study the effect of the tea of Example 4 on their physiological responses to stress. We created stressful situations in the experimental laboratory that elicited the appropriate cardiovascular responses (the laboratory provided a setting in which strict environmental control was exerted).

First, the patients played the Super Pong video game. Heart rate and blood pressure of each patient prior to and at the end of the game were measured. An average heart rate increase of 20.6 bpm and an average blood pressure increase of 35/20 mm Hgs were found immediately at the end of completing the video game.

Additionally, the Space Invaders game was played by each patient and the heart rate and blood pressure were measured at the end of the game. A mean heart rate increase of 21.9 bpm and a mean blood pressure increase of 40/26 mm Hgs were found immediately at the end of the game.

After a couple of hours of relaxation the Group C patients' heart rate and blood pressure were measured again so as to establish a base line with which subsequent measurements were to be compared. Next, the subjects were tested again using the above-described video games as follows: at the point where an average heart rate increase of an additional 15 beats per minute and 20/15 mm Hgs as compared to the base line measurement, the subjects were given a cup of the tea of Example 4 to imbibe while continuing to play the video games. Although the games, especially the Space Invaders game, became more difficult the longer played, within 20 minutes of consuming the tea the subjects' heart rates and blood pressures began to decline gradually, reaching normalcy, i.e., base line figures, within 30 minutes while the subjects continued playing the games.

The patients were then denied the use of the composition of the present invention for two weeks so that a solid oral formulation could be tested and the result compared with that collected using the tea formulation of the present invention.

After the elapse of two weeks the three groups A, B and C were tested again as described in connection with the use of the Example 4 formulation. At this time, however, the capsules of Example 1 of the present invention were used. After adjusting for slower bioavailability of the capsules and absorption into the blood stream, essentially the same results were obtained as with the Example 4 formulation.

Variations and changes may be made by those skilled in the art without departing from the spirit of the invention.

What is claimed is:

1. An oral pharmaceutical composition for reducing heart rate and blood pressure due to stress in a mammal consisting essentially of freeze-dried soluble components of borage petals obtained by extraction of said soluble components with a solvent selected from the group consisting of acetone, methyl ethyl ketone and diethyl ketone.

2. The oral pharmaceutical composition of claim 1 wherein said freeze-dried extract of borage petals is packed in a primary porous woven or non-woven paper bag and a secondary, air-tight plastic bag and vacuum-sealed.

3. A method for reducing heart rate and blood pressure due to stress in a mammal comprising administering to said mammal a heart rate and blood pressure reducing effective amount of a pharmaceutical composition consisting essentially of freeze-dried soluble components of borage petals obtained by extraction of said soluble components with a solvent selected from the group consisting of acetone, methyl ethyl ketone and diethyl ketone.

4. The method of claim 3 wherein said effective amount of said pharmaceutical composition is in a dose range of from about 5 to about 100 gm/kg of body weight/day.

5. The method of claim 4 wherein said dose range is of from about 25 to 60 gm/kg of body weight/day.

6. The method of claim 3 wherein said stress is associated with circulatory heart diseases selected from the group consisting of angina, palpitations and hypertension.

* * * * *